United States Patent [19]

Puckette

[11] Patent Number: 5,061,669

[45] Date of Patent: Oct. 29, 1991

[54] PREPARATION OF BIARYL COMPOUNDS

[75] Inventor: Thomas A. Puckette, Longview, Tex.

[73] Assignee: Eastman Kodak Company, Rochester, N.Y.

[21] Appl. No.: 463,745

[22] Filed: Jan. 12, 1990

Related U.S. Application Data

[60] Division of Ser. No. 389,022, Aug. 3, 1989, Pat. No. 4,916,227, which is a continuation-in-part of Ser. No. 277,826, Nov. 30, 1988, abandoned.

[51] Int. Cl.$^5$ .............................................. B01J 31/24
[52] U.S. Cl. ...................................... 502/167; 502/162
[58] Field of Search ................................ 502/162, 167

[56] References Cited

U.S. PATENT DOCUMENTS 4,263,466 4/1981 Colon et al. .................... 502/162 X
4,326,989 4/1982 Colon et al. ....................... 502/162

Primary Examiner—Patrick P. Garvin
Attorney, Agent, or Firm—J. Frederick Thomsen; William P. Heath, Jr.

[57] ABSTRACT

A method for the preparation of biaryl compounds is disclosed which comprises contacting an aromatic halide in the presence of a catalyst comprising zerovalent nickel, a bidentate phosphorus-containing coordinating ligand and a reducing metal in a polar, aprotic solvent system for a time and under conditions suitable for the formation of biaryl compound.

24 Claims, No Drawings

PREPARATION OF BIARYL COMPOUNDS

This application is a divisional of copending application Ser. No. 07/389,022 filed Aug. 3, 1989, now U.S. Pat. No. 4,916,227, which was a continuation-in-part of application Ser. No. 07/277,826 filed Nov. 30, 1988, now abandoned.

The present invention relates to the preparation of biaryl compounds from aryl halides. In a particular aspect, the present invention relates to the reductive coupling of aryl halides.

BACKGROUND OF THE INVENTION

It is known that biphenyl compounds can be produced by the reductive coupling of aryl halides. For example, Chao, et al., in the *Journal of Organic Chemistry*, Volume 48, at pages 4904–4907 (1983), disclose the reaction of aryl halides with an equivalent amount of a highly activated metal such as nickel powder.

An alternative approach is to activate an aryl halide by a chemical transformation, and then allow the activated aryl halides to couple to form biaryl species. For example, Gilman, et al., in the Journal of the American Chemical Society, Volume 61, at pages 957–959 (1939), demonstrated this approach by the reaction of two equivalents of aryl Grignard reagents with one equivalent of nickel(II) salts to give biaryl compounds. This reaction is believed to proceed through the bis(aryl)-nickel(0) species which then decomposes to give the desired biaryl product.

Kumada, et al., in *Bulletin of the Chemical Society of Japen*, Volume 49, at pages 1958–1969 (1976), have demonstrated that aryl halides can be reacted with a variety of aliphatic Grignard reagents to give alka-aryl products. However, attempts to couple aryl Grignard reagents with aryl halides were successful only with aryl bromides. Attempts to use aryl chlorides gave less than a ten percent yield of desired biaryl products.

Aryl chlorides are frequently more readily available than are the corresponding bromides and iodides. The chlorides are also typically less reactive and are less expensive materials as well. It would, therefore, be desirable to find a means to promote the coupling of aryl chlorides to produce high yields of biaryl compounds.

Such coupling of aryl chlorides has been disclosed by Colon, et al., in U.S. Pat. No. 4,263,466. The authors disclose the use of a metallic reducing agent such as zinc, magnesium, or manganese in a dipolar, aprotic solvent such as dimethylformamide with a catalyst containing a nickel compound in combination with triaryl organophosphines and alkali metal halide promoters. The reducing metal converts the nickel salts into highly reactive zerovalent nickel compounds which promote the coupling of the aryl halides and regenerate the nickel salts which can be reduced again to the zerovalent state, thereby maintaining the catalytic cycle.

In later publications by the same authors (see Colon, et al., in *Journal of Organic Chemistry*, Vol. 51 at pages 2627–2637 (1986), it is indicated that bidentate ligands (as opposed to the monodentate triaryl organophosphines disclosed in '466) are not effective for the nickel/reducing metal-promoted reductive coupling reaction. Takagi, et al., in the *Bulletin of the Chemical Society of Japan*, at pages 1887–1890 (1984) have made similar observations. See especially Run Number 14 reported at page 1888.

STATEMENT OF THE INVENTION

In accordance with the present invention, it has surprisingly been found that aryl chlorides can be reductively coupled employing bidentate ligands to produce biaryl compounds in high yield. By contacting aryl halides with a catalyst comprising a nickel compound, at least one bidentate phosphorus-containing ligand selected from a specified group and a reducing metal, high yields of biaryl compounds are obtained.

The practice of the present invention allows for the ready preparation of biaryl derivatives from aryl chloride starting materials. Aryl chlorides are generally preferred starting materials as they are more accessible on a commercial basis and are generally less expensive than the corresponding aryl bromides or aryl iodides.

DETAILED DESCRIPTION OF THE INVENTION

In accordance with the present invention, there is provided a method for the preparation of biaryl compounds of the structure:

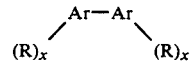

wherein Ar is an aromatic moiety having in the range of 4 up to 20 carbon atoms, each R is independently selected from alkyl, aryl, —F, —NR'$_2$, —CN, —CHO, —OR', —OCO—R', —COO—R',

—SO$_2$—R', —SO$_3$R', or —NR'COR':
wherein R' is a hydrocarbyl or heteroaryl radical having up to 20 carbon atoms, and x is an integer falling in the range of 0 up to 8, depending on the size of the aromatic ring, Ar, and with the proviso that there be no more than one substituent ortho to the Ar—Ar bond.

The invention method comprises contacting an aromatic halide having the structure:

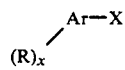

wherein Ar, R and x are as defined above and X is a halogen; under conditions suitable for the formation of the desired biaryl compound in the presence of at least 0.001 equivalents of a nickel catalyst comprising:

I) an anhydrous nickel compound,
II) at least one bidentate phosphorus-containing ligand selected from the group consisting of:

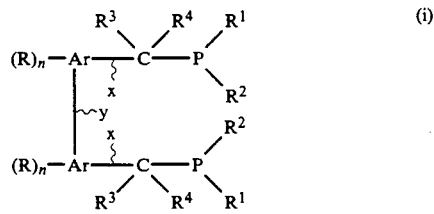

wherein each Ar is independently selected from aromatic ring compounds having 6 up to 14 carbon atoms, e.g., phenyl, naphthyl, phenanthryl or anthracenyl;

the x bonds and the y bonds are attached to adjacent carbon atoms on the ring structures;

each R, when present as a substituent, is independently selected from alkyl, aryl, —F, —NR'$_2$, —CN, —CHO, —OR', —OCO—R', —COO—R',

—SO$_2$—R', —SO$_3$—R', or —NR'COR':
wherein
R' is a hydrocarbyl or heteroaryl radical having up to 20 carbon atoms;

n is a whole number in the range of 0–4 where Ar is phenyl; 0–6 where Ar is naphthyl; and 0–8 where Ar is phenanthryl or anthracenyl;

each R$^1$ and R$^2$ is independently selected from alkyl, aryl, aralkyl, alkaryl or cycloaliphatic radicals, or substituted derivatives thereof wherein substituted derivatives include ethers, amines, amides, sulfonic acids, esters, hydroxyl groups and alkoxy groups;

each R$^3$ and R$^4$ is independently selected from hydrogen and the R$^1$ substituents;

each of the above alkyl groups or moieties is straight or branched chain of 1–20 carbons;

each aryl group contains 4–20 ring carbons; and each cycloaliphatic group contains from 4–8 ring carbons;

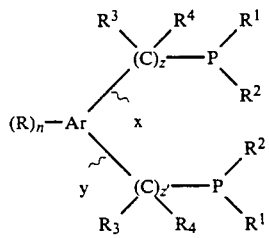

wherein Ar, x, y, R, n, R$^1$, R$^2$, R$^3$, and R$^4$ are each as defined above, and each of z and z' can independently vary between 0 and 4, with the provisio that z+z' is at least 2;

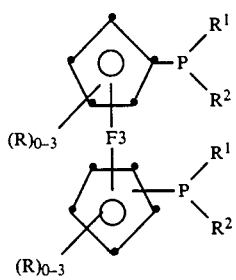

wherein R, R$^1$ and R$^2$ are defined above; and

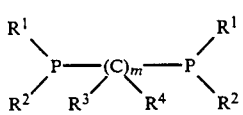

wherein R$^1$, R$^2$, R$^3$, and R$^4$ are as defined above; and m is a whole number which can vary from 4 up to 8; preferably from 5 up to 8; as well as mixtures of any two or more of said type (i), (ii), (iii), (iiii), or (iv) organophosphines; and (III) at least one reducing metal selected from the group consisting of zinc, magnesium and maganese, wherein said contacting is carried out in a polar, aprotic, solvent system for a time and under conditions suitable for the formation of the desired biaryl compound.

Reaction temperatures employed in the practice of the present invention can vary widely. Typically, reaction temperatures fall in the range of about 0° up to 250° C., with reaction temperatures in the range of about 25° up to 120° C. being preferred.

Reaction times contemplated for the practice of the present invention can vary widely. One of skill in the art can readily determine that amount of time which is sufficient to allow formation of the desired biaryl or heterobiaryl compounds. Typically, reaction times will fall in the range of about 0.1 up to 24 hours or longer, with reaction times in the range of about 0.5 up to 16 hours being preferred.

Aryl halides contemplated for use in the practice of the present invention are conpounds have the general structure:

wherein Ar is an aromatic moiety having in the range of 4 up to 20 atoms, each R is independently selected from alkyl, aryl, —F, —NR'$_2$, —CN, —CHO, —OR', —OCO—R',

—SO$_2$R', SO$_3$R', or NR'COR':
wherein R, is a hydrocarbyl or heteroary radical having up to 20 carbon atoms; X is a halogen and x is an integer falling in the range of 0 up to 8, depending on the size of the aromatic ring, Ar, and with the further proviso that there be no more than one substituent ortho to the halogen moiety. Exemplary aryl halides contemplated for use in the practice of the present invention include:

2-chlorotoluene,
2-bromotoluene,
4-chlorotoluene,
4-bromotoluene,
2-chloro-4-methylnaphthalene,
2-bromo-4-methylnaphthalene,
4-chloroanisole,
4-bromoanisole,
4-chlorophenylacetate,
4-bromophenylacetate,
2-chlorobenzyl(2-methoxy)ethyl ether,
2-bromobenzyl(2-methoxy)ethyl ether,
2-chlorobenzyl methyl ether,
2-bromobenzyl methyl ether,
2-chlorobenzyl ethyl ether,
2-bromobenzyl ethyl ether,
2-chlorothiophene,
2-bromothiophene,
2-chloropyridine,
2-bromopyridine, 2-chloro-3-methylnaphthalene,
2-bromo-3-methylnaphthalene,
1-chloro-2-methylnaphthalene,
1-bromo-2-methylnaphthalene,
1-methyl-2-chloronaphthalene,
1-methyl-2-bromonaphthalene,
4-fluoro-2-chlorotoluene,
4-fluoro-2-bromotoluene,
4-(N-ethyl-N-acetyl)-2-chlorotoluene,
4-(N-ethyl-N-acetyl)-2-bromotoluene,
6-(N-ethyl-N-acetyl)-2-chlorotoluene,
6-(N-ethyl-N-acetyl)-2-bromotolue and the like, as well as mixtures of any two or more thereof.

Presently preferred monohalides contemplated for use in the practice of the present invention include compounds having the structural formula:

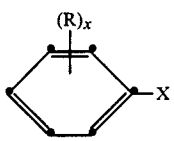
(I)

wherein one or more of the carbon atoms of the benzene ring rn formula (I) is optionally replaced by N;

wherein X is a halogen selected from the group consisting of Cl, Br and I;

R is a monovalent radical selected from alkyl, aryl, —F, —NR′$_2$, —CN, —CHO, —OR′, —OCO—R, —COO—R′,

—SO$_2$—R′, —SO$_3$—R′, or —NR′COR′:

wherein R′ is a hydrocarbyl or heteroaryl radical having up to 20 carbon atoms,and x is an integer having values of 0 to 4 with the proviso that no more than one R is in a position ortho to the X-containing ring carbon atom.

Additional compounds contemplated by the above structural formula are those wherein one or more of the carbon atoms of the benzene ring is replaced by N. Especially preferred compounds contemplated by the above formula are those wherein X is Cl.

Examples of preferred monohalides which satisfy structural formula (I) include:
2-chlorotoluene,
2-chloropyridine,
4-fluoro-2-chlorotoluene,
2-chlorobenzyl methyl ether,
2-chlorobenzyl ethyl ether,
4-(N-ethyl-N-acetyl)-2-chlorotoluene,
6-(N-ethyl-N-acetyl)-2-chlorotoluene,
4-chlorotoluene,
4-chloroanisole,
2-chlorobenzyl(2-methoxy)ethyl ether,
as well as mixtures of any two or more thereof.

A wide range of nickel compounds are suitable for use in the practice of the present invention, so long as the nickel compounds employed are essentially water-free. The nickel(II) halide salts are a convenient source of nickel as such compounds are readily available in anhydrous form. Alternatively, hydrates of such compounds can be employed if an appropriate means of water removal, e.g., azeotropic distillation, is employed prior to contacting the nickel species with the reducing metal and aryl halide. Those of skill in the art recognize that a wide variety of nickel compounds can be used in addition to the nickel(II) halides, e.g., nickel nitrates, sulfates, phosphates, oxides, carbonates, carboxylates, acetylacetonate and the like, as well as Ni(O) complexes such as, for example, bis(1,5-cyclooctadienyl)nickel(O), nickel(0) tetracarbonyl, and the like.

The nickel(II) halides are presently preferred because of their ready availability in anhydrous form (or, alternatively, the ease with which the hydrates forms such compounds can be dehydrated), and because the presence of halides in the reaction mixture appears to promote the coupling reaction. Especially preferred are nickel chloride and nickel bromide.

Suitable ratios of nickel to aryl halides can vary widely. Molar ratios in the range of 0.0001 up to 0.5:1 are generally suitable. Ratios in the range of about 0.01 up to 0.2:1 are preferred, with molar ratios in the range of about 0.03 up to 0.1 being most preferred because good conversions are obtained at reasonable reaction rates.

Optionally added to the catalyst composition are inorganic salt promoters. When used, preferred promoters include alkali, alkaline earth, zinc, magnesium, manganese and aluminum halides, or mixtures thereof. Bromides are particularly preferred. The amount of promoter, when used, can range from about 0.1 to about 1000 moles per gram atom of nickel with about 1 to about 100 moles of promoter being preferred.

The presently most preferred promoters include alkali metal iodides, alkali metal bromides and alkali metal chlorides.

Organophosphines contemplated for use in the practice of the present invention are compounds having the structures set forth above as (i), (ii), (iii), or (iv).

Exemplary compounds contemplated by structure (i) include compounds having the structural formula:

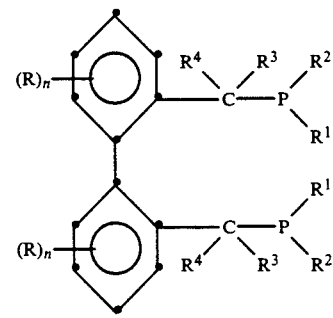

wherein R, R$^1$, R$^2$, R$^3$, R$^4$, and n are as defined above; including such compounds as:
2,2′-bis(diphenylphosphinomethyl)-1,1′-biphenyl;
2,2′-bis(dibenzylphosphinomethyl)-1,1′-biphenyl;
2,2′-bis(phenylbenzylphosphinomethyl)-1,1′-biphenyl; and
2,2′-bis(diisobutylphosphinomethyl)-1,1′-biphenyl.

Exemplary compounds contemplated by structure (i) also include compounds having the structural formula:

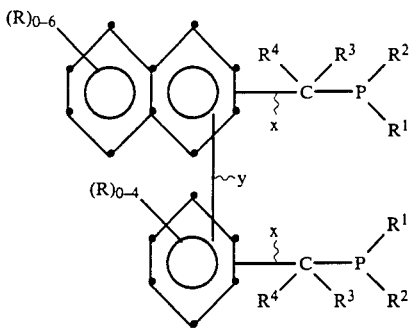

wherein R, $R^1$, $R^2$, $R^3$, $R^4$, x and y are defined above; such as, for example
2-(diphenylphosphinomethyl)-1-[2-(diphenylphosphino-methyl)phenyl]naththalene.

Exemplary compounds contemplated by structure (i) also include compounds having the structural formula:

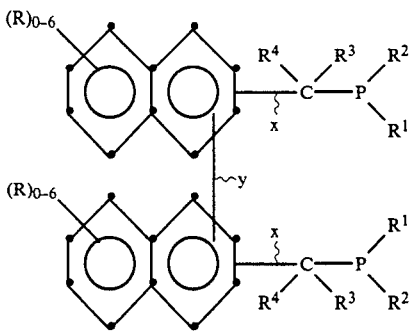

wherein R, $R^1$, $R^2$, $R^3$, $R^4$, x and y are defined above; such as, for example
2,2'-bis(diphenylphosphinomethyl)-1,1;-binaphthyl.

Exemplary compounds contemplated by structure (ii) include compounds having the structural formula:

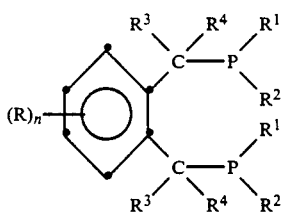

wherein R, $R^1$, $R^2$, $R^3$, $R^4$ and n are as defined above; such as, for example
α,α'-bis(diphenylphosphino)ortho-xylene.

Exemplary compounds contemplated by structure (ii) also include compounds having the structural formula:

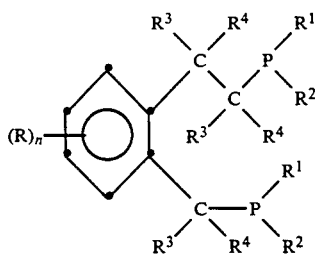

wherein R, $R^1$, $R^2$, $R^3$, $R^4$ and n are as defined above; such as, for example
α, β'-bis(diphenylphosphino)-2-ethyltoluene.

Exemplary compounds contemplated by structure (ii) also include compounds having

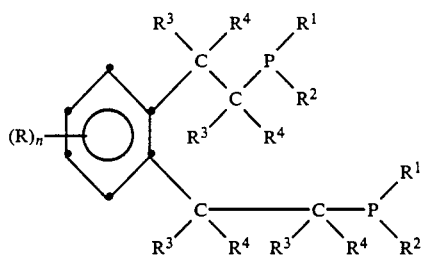

wherein R, $R^1$, $R^2$, $R^3$, and $r^4$ and n are as defined
1,2-bis[2-(diphenylphosphino)ethyl]benzene.

Exemplary compounds contemplated by structure (iii) include: 1,'-bis(diphenylphosphino)ferrocene, and the like.

Exemplary compounds contemplated by structure (iv) include:
1,4-bis(diphenylphosphino)butane,
1,5-bis(diphenylphosphino)pentane, and
1,6-bis(diphenylphosphino)hexane;
as well as mixtures of any two or more thereof. Also contemplated are mixtures of any two or more of said type (i), (ii), (iii) or (iv) organophosphines.

The molar ratio of organophosphine to nickel compound employed in the practice of the present invention can vary widely. Typically, such molar ratio will fall within the range of 0.5:1 up to 20:1, with ratios in the range of 1:1 up to 10:1 preferred. Ratios in the range of about 1:1 up to 3:1 are presently most preferred because little added benefit is seen in the use of large excesses of organophosphine(s).

Optional coordinating ligands employed in combination with the above-described bidentate organophosphines are bidentate ligands containing at least one nitrogen atom as part of an aromatic ring structure. Such bidentate ligands include bipyridine, a $C_1$ up to Cdialkylamino pyridine, phenanthroline or 2.picolinic acid, and the like.

When the optional use of mixtures of bidentate organophosphine and bidentate ligand containing at least one nitrogen atom as part of an aromatic ring structure are employed as the coordinating ligand, molar ratios of the bidentate organophosphine to the bidentate ligand containing at least one nitrogen atom as part of an aromatic ring structure can vary widely, for example, in the range of about 0.1:1 up to 20:1, with ratios in the range of 0.5 up to 10 preferred. Ratios in the range of about 1:1 up to 2:1 are presently most preferred because little added benefit is observed when large excesses of the bidentate ligand containing at least one nitrogen atom as part of an aromatic ring structure are employed.

Solvents suitable for use in the practice of the present invention include dipolar, aprotic solvents such as solvents, such as N,N-dimethylacetamide, N,N-dimethylformamide, 1-methyl-2-pyrrolidinone, tetramethylurea, dimethylsulfoxide, sulfolane, and the like. If desired these dipolar, aprotic solvents can be mixed with lower polarity inert solvents, such as saturated aliphatic hydrocarbons, including pentanes, hexanes, dodecanes and the like; aromatic hydrocarbons, such as benzene, toluene, xylenes and the like; and saturated aliphatic and cycloaliphatic ethers, such as, diethyl ether, diglyme, tetrahydrofuran and the like.

It is preferred that all solvents use in the practice of this invention be anhydrous.

Although magnesium and manganese metals can be used, zinc metal is the presently preferred reducing metal for use in the invention process for coupling aryl monochlorides.

The molar ratio of reducing metal to aryl halide employed in the practice of the present invention can vary widely. Typically, such molar ratio will fall within the range of about 0.01:1 up to 20:1, with ratios in the range of about 0.2:1 up to 10:1 preferred. Ratios in the range of about 0.4:1 up to 5:1 are presently most preferred because it is desired to minimize the quantity of reducing metal which must be removed from the reaction mixture and little added benefit is obtained when large excesses of reducing metal are employed.

The molar ratio of reducing metal to nickel employed in the practice of the present invention can vary widely. Typically, such molar ratios will fall within the range of about 1 up to 1000:1, with ratios in the range of about 10 up to 500:1 being preferred. Ratios in the range of about 40 up to 100:1 are presently preferred for the same reasons as stated in the preceding paragraph.

Preparation of the novel catalyst composition is carried out conveniently by mixing the aforementioned nickel compound, ligand(s), promoter, and reducing metal(s) in the dipolar, aprotic solvent under an inert atmosphere and heating to a temperature in the range of about 25° to about 80° C.

The present invention will now be described in greater detail by reference to the following non-limiting examples.

EXAMPLES

All reactions were conducted under an inert atmosphere. Glassware was dried prior to use and flushed with nitrogen. Commercial materials were used when possible and the following were used as purchased: Anhydrous nickel(II) bromide, sodium bromide, anhydrous dimethylformamide, and zinc powder (−325 mesh). Organophosphine ligands were purchased or prepared by methods known by those of skill in the art.

Typical Experimental Procedure

Nickel(II) bromide (0.22 g, 1 mmol), the desired phosphine ligand (1.5 to 3 mmol), sodium bromide (3 g), anhydrous dimethylformamide (DMF; 15 mL), zinc powder (3 g, 45 mmol) and an aryl halide (20 mmoles) were combined under a nitrogen atmosphere and heated to 70° C. for 14 to 16 hours. The mixture was cooled to ambient and analyzed by conventional chromatography techniques. In those cases where the DMF solvent may obscure one of the products, the reaction mixture was partitioned between aqueous ammonium chloride and ethyl acetate. The organic phase was then analyzed by normal procedures.

Results of numerous runs with different aryl halides and different phosphine ligands are summarized in Tables I, II and III.

TABLE I

Reductive Dimerization of 2-Chlorotoluene Using Linear Bidentate Phosphines. $(Ph)_2P-(CH2)_m-P(Ph)_2$*

| Phosphine m = | Mmole Ligand | [P]/[Ni][1] | % Convn of 2-CT[2] | % Selectivity, 2,2'-Bitolyl |
|---|---|---|---|---|
| 1 | 1.5 | 3 | 0 | 0 |
| 2 | 1.5 | 3 | 24.9 | 97.8 |
| 3 | 1.5 | 3 | 9.4 | 100 |
| 4 | 1.5 | 3 | 100 | 94.9 |
| 5 | 1.5 | 3 | 100 | 96.1 |
| 6 | 1.5 | 3 | 100 | 95.4 |

*All runs were carried out at 70° C. for 16 hours using 1 mmol $NiBr_2$, 30 mmol zinc, 3.0 grams of NaBr, 20 mmol of 2-CT in 15 mL DMF and ligand as noted.
[1] Atomic ratio of phosphorus to nickel.
[2] 2-CT = 2-chlorotoluene These results demonstrate that for linear bidentate phosphines of the type (iv), m must be at lest 4, i.e., there must be at least 4 carbon atoms in the chain between the phosphate units. Chain lengths longer than 4 carbon atoms are seen to be particularly effective.

TABLE II

Reductive Dimerization of Halotoluenes to Bitolyls*

| Aryl Halide | % Convn | % Selectivity to Toluene | % Selectivity to Dimers | % Expected Dimer |
|---|---|---|---|---|
| 2-Chlorotoluene | 100 | <0.5 | 100 | 98.9[1] |
| 2-Bromotoluene | 100 | 4.85 | 95.15 | 97.7[1] |
| 3-Iodotoluene | 100 | 10.8 | 89.2 | 80.4[2] |

*All runs were conducted at 70° C. for 16 hours using 1 mmol $NiBr_2$, 30 mmol zinc, 20 mmol aryl halide, 3.0 g of NaBr in DMF (15 mL). The ligand for all of these runs was 2,2'-bis(diphenylphosphinomethyl)-1,1'-biphenyl (BISBI; 1.5 mmol).
[1] Expected dimeric product is 2,2'-bitolyl.
[2] Expected dimeric product is 3,3'-bitolyl.

These results demonstrate that aryl chlorides are preferred starting materials for the invention reductive coupling reaction because they give the desired products in high yields with very high selectively, without producing significant levels of reduced mono-aromatic product (i.e., toluene) or isomerized product (e.g., 2,3'-bitolyl).

TABLE III

The Reductive Dimerization of Substituted Aryl Halides to Substituted Biaryl Derivatives*

| Aryl Halide | Ligand[1] | % Convn | % Selectivity[2] H-Aryl | % Selectivity[2] Dimers | % Expected Isomeric Dimer[3] |
|---|---|---|---|---|---|
| 4-Bromoanisole | OXYL | 100 | 11.4 | 88.6 | 62.7 |
| 4-Bromoanisole | BISBI | 99.7 | 4.6 | 95.4 | 75.3 |
| 4-Chlorobenzotrifluoride | OXYL | 85.9 | 3.7 | 96.3 | 98.7 |
| 4-Chlorobenzotrifluoride | BISBI | 100 | 2 | 98 | 98.7 |
| 4-Chlorobenzonitrile | OXYL | 100 | 16.5 | 83.5 | 79.7 |
| 4-Chlorobenzonitrile | BISBI | 100 | 5.2 | 94.8 | 72.9 |
| Methyl-3-chlorobenzoate | OXYL | 100 | 7.9 | 92.1 | 93.3 |
| Methyl-3-chlorobenzoate | BISBI | 100 | 3.8 | 96.2 | 89.2 |
| 2-Chloroacetophenone | OXYL | 88.9 | 43.2 | 56.8 | 66.6 |

TABLE III-continued

The Reductive Dimerization of Substituted Aryl Halides to Substituted Biaryl Derivatives*

| Aryl Halide | Ligand[1] | % Convn | % Selectivity[2] H-Aryl | Dimers | % Expected Isomeric Dimer[3] |
|---|---|---|---|---|---|
| 2-Chloro-acetophenone | BISBI | 100 | 9.5 | 90.5 | 54.5 |
| 4-Chlorobenzaldehyde | OXYL | 100 | 60 | 40 | 100 |
| 4-Chlorobenzaldehyde | BISBI | 100 | 19.7 | 80.3 | 100 |
| 1-Bromo-2-methyl-naphthalene | BISBI | 28.8 | 3.6 | 96.4 | 100 |
| 1-Bromo-3-fluorobenzene | BISBI | 100 | <0.5 | 99.5 | 100 |

*All runs were carried out at 70° C. for 16 hours using 1 mmol NiBr$_2$, 30 mmol zinc, 20 mmol aryl halide, 3.0 g NaBr, 1.5 mmol of ligand in DMF (15 mL).
[1])OXYL = α,α'-bis(diphenylphosphino)ortho-xylene.
BISBI = 2,2'-bis(diphenylphosphinomethyl)-1,1'-biphenyl
[2])H-Aryl is the reduction product of the aryl halide wherein the halogen has been replaced with a hydrogen.
Dimers refers to all aromatic-aromatic coupling products.
*[3])Expected isomeric dimer of:
4-bromoanisole is 4,4'-dimethoxybiphenyl;
4-chlorobenzotrifluoride is 4,4'-bis(trifluoromethyl)biphenyl;
4-chlorobenzonitrile is 4,4'-dicyanobiphenyl;
methyl-3-chlorobenzoate is the dimethyl ester of 3,3'-diphenyldicarboxylic acid;
2-chloroacetophenone is 2,2'-diacetylbiphenyl;
4-chlorobenzaldehyde is 4,4'-diphenyldicarboxaldehyde;
1-bromo-2-methylnaphthalene is 2,2'-dimethyl-1,1'-binaphthyl; and
1-bromo-3-fluorobenzene is 3,3'-difluorobiphenyl.

The data in Table III demonstrate that a wide variety of functional groups are compatible with the invention process.

The invention has been described in detail with particular reference to preferred embodiments thereof, but it will be understood that variations and modifications can be effected within the spirit and scope of the invention.

We claim:

1. A catalytically active combination comprising:
   (I) an anhydrous nickel compound,
   (II) at least one bidentate phosphorus-containing ligand selected from the group consisting of

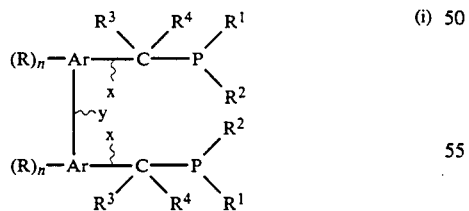

(i)

wherein
each Ar is independently selected from aromatic ring compounds having 6 up to 14 carbon atoms;
the x bonds and the y bonds are attached to adjacent carbon atoms on the ring structures;
each R, when present as a substitutent is independently selected from alkyl, aryl, —F, —NR'$_2$, —CN, —CHO, —OR', -OCO—R', —COO—R',

—SO$_2$—R', —SO$_3$—R', or —NR'COR';
wherein R' is a hydrocarbyl or heteroaryl radical having up to 20 carbon atoms;
n is an integer in the range of 0–4 where Ar is phenyl; 0–6 where Ar is naphthyl; and 0–8 where Ar is phenanthryl or anthracentyl;
each R$^1$ and R$^2$ is independently selected from alkyl, aryl, aralkyl, alkaryl or cycloaliphatic radicals, or substituted derivatives thereof wherein substituted derivatives are ethers, amines, amides, sulfonic acids, esters, hydroxyl groups and alkoxy groups;
each R$^3$ and R$^4$ is independently selected from hydrogen and the R$^1$ substituents;
each of the above alkyl groups or moieties is straight or branched chain of 1–20 carbons;
each aryl group contains 6–20 ring carbons; and
each cycloaliphatic group contains from 4–8 ring carbons;

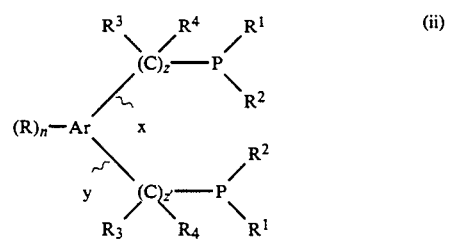

(ii)

wherein Ar, x, y, R, n, R$^1$, R$^2$, R$^3$, and R$^4$ are each as defined above, and each of z and z' can independently vary between 0 and 4, with the proviso that z+z' is at least 2;

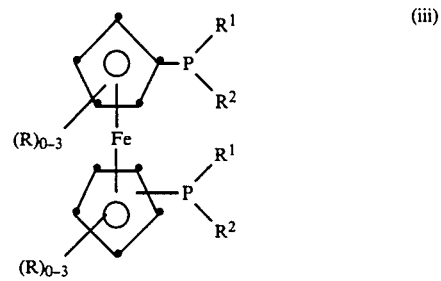

(iii)

wherein R, R$^1$ and R$^2$ are defined above; and

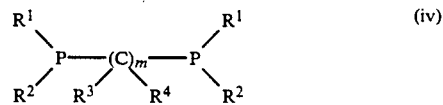

(iv)

where R$^1$, R$^2$, R$^3$, and R$^4$ are as defined above; and m is a whole number which can vary from 5 up to 8;
as well as mixtures of any two or more of said type (i), (ii), (iii), or (iv) organophosphines; and
(III) at least one reducing metal selected from the group consisting of zinc, magnesium and manganese;

wherein the amount of bidentate phosphorus-containing ligand falls within the range of 0.5 up to 20 moles per gram atom of nickel; and wherein the amount of reducing metal falls within the range of about 1 up to 1000 moles per mole of nickel.

2. The combination of claim 1 wherein said bidentate ligand has the structural formula:

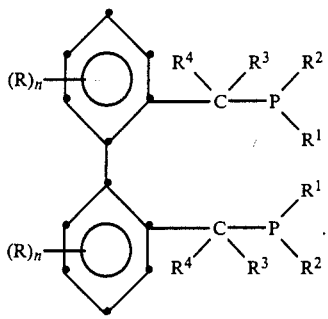

3. The combination of claim 1 wherein said bidentate ligand has the structural formula:

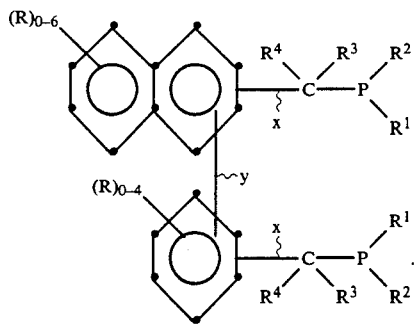

4. The combination of claim 1 wherein said bidentate ligand has the structural formula:

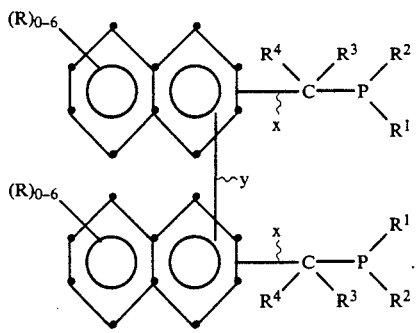

5. The combination of claim 1 wherein said bidentate ligand has the structural formula:

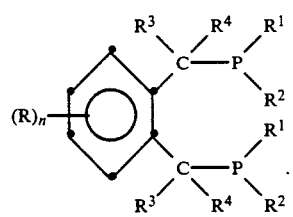

6. The combination of claim 1 wherein said bidentate ligand has the structural formula:

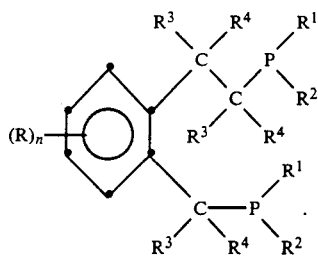

7. The combination of claim 1 wherein said bidentate ligand has the structural formula:

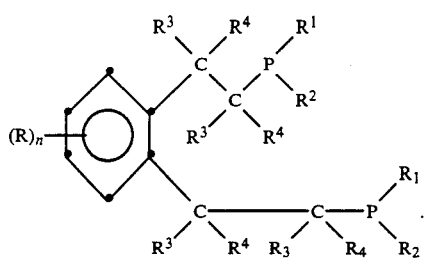

8. The combination of claim 1 wherein said bidentate ligand has the structural formula:

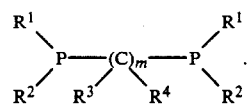

9. The combination of claim 1 further comprising at least 0.1 moles per gram atom of nickel of an inorganic salt selected from the group consisting of:
   alkali metal iodides,
   alkali metal bromides,
   alkali metal chlorides,
as well as mixtures of any two or more thereof.

10. The combination of claim 2 wherein said bidentate ligand is selected from the group consisting of:
2,2'-bis(diphenylphosphinomethyl)-1,1'-biphenyl;
2,2'-bis(dibenzylphosphinomethyl)-1,1'-biphenyl;
2,2'-phenylbenzylphosphinomethyl)-1,1'-biphenyl; and
2,2'-bis(diisobutylphosphinomethyl)-1,1'-biphenyl.

11. The combination of claim 1 wherein said bidentate ligand has the structural formula:

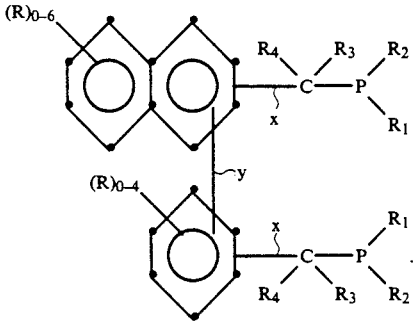

12. The combination of claim 1 wherein said bidentate ligand is 2-(diphenylphosphinomethyl)-1-[2-(diphenylphosphinomethyl)phenyl]naphthalene.

13. The combination of claim 4 wherein said bidentate ligand is 2,2'-bis(diphenylphosphinomethyl)-1,1'-binaphthyl.

14. The combination of claim 5 wherein said bidentate ligand is α, α'-bis(diphenylphosphino)ortho-xylene.

15. The combination of claim 6 wherein said bidentate ligand is α,β'-bis(diphenylphosphino)-2-ethyltoluene.

16. The combination of claim 7 wherein said bidentate ligand is 1,1'-bis(diphenylphosphino)ferrocene.)zene.

17. The combination of claim 1 wherein said bidentate ligand is 1,1'-bis(diphenylphosphino)ferrocene.

18. The combination of claim 1 wherein said bidentate ligand is selected from the group consisting of:
1,4-bis(diphenylphosphino)butane,
1,5-bis(diphenylphosphino)pentane,
1,6-bis(diphenylphosphino)hexane,
as well as mixtures of two or more thereof.

19. The combination of claim 1 wherein said catalytic combination further comprises at least one bidentate ligand containing at least one nitrogen atom as part of an aromatic ring structure.

20. The combination of claim 19 wherein said bidentate ligand containing at least one nitrogen atom is selected from 2,2'-bipyridine, a $C_1$ up to $C_6$ dialkylamino pyridine, phenanthroline or 2-picolinic acid.

21. The combination of claim 1 wherein said reducing metal is zinc.

22. The combination of claim 1 wherein the nickel compound is nickel chloride.

23. The combination of claim 1 wherein the amount of bidentate phosphorus-containing ligand falls in the range of about 1 up to 10 moles per gram atom of nickel; and the molar ratio of reducing metal to nickel falls in the range of about 10 up to 500:1.

24. The combination in accordance with claim 1 wherein the amount of bidentate phosphorus-containing ligand falls in the range of about 1 up to 3 moles per gram atom of nickel; and the molar ratio of reducing metal to nickel falls in the range of about 40 up to 100:1.

* * * * *